United States Patent
Bue, Jr.

(10) Patent No.: US 9,480,592 B2
(45) Date of Patent: *Nov. 1, 2016

(54) TOPICAL PROPRIOCEPTIVE ACL TUBE AND METHODS OF USE

(71) Applicant: TOPICAL GEAR, LLC, Austin, TX (US)

(72) Inventor: William D. Bue, Jr., Austin, TX (US)

(73) Assignee: Topical Gear, LLC, Lakeway, TX (US)

( * ) Notice: Subject to any disclaimer, the term of this patent is extended or adjusted under 35 U.S.C. 154(b) by 741 days.

This patent is subject to a terminal disclaimer.

(21) Appl. No.: 13/796,914

(22) Filed: Mar. 12, 2013

(65) Prior Publication Data

US 2013/0190665 A1   Jul. 25, 2013

Related U.S. Application Data

(63) Continuation-in-part of application No. PCT/US2012/039748, filed on May 25, 2012.

(60) Provisional application No. 61/490,020, filed on May 25, 2011.

(51) Int. Cl.
*A61F 13/00* (2006.01)
*A61F 5/01* (2006.01)
(Continued)

(52) U.S. Cl.
CPC .......... *A61F 5/0123* (2013.01); *A61F 5/0109* (2013.01); *A61F 5/30* (2013.01); *A61H 1/006* (2013.01)

(58) Field of Classification Search
CPC ........ A61F 13/061; A61F 13/14; A61F 5/01; A61F 5/0109; A61F 5/0123; A61F 13/00
USPC ................................................ 602/23, 60–62
See application file for complete search history.

(56) References Cited

U.S. PATENT DOCUMENTS

| 4,084,584 A | 4/1978 | Detty |
| 4,445,505 A * | 5/1984 | Labour ................. A61F 5/0109 602/26 |

(Continued)

FOREIGN PATENT DOCUMENTS

| DE | 9417221 U1 | 1/1995 |
| EP | 0 262 638 A2 | 4/1988 |

OTHER PUBLICATIONS

International Search Report for PCT/US2012/039748 dated Sep. 21, 2012.

(Continued)

*Primary Examiner* — Kim L Lewis
(74) *Attorney, Agent, or Firm* — Rodney J. Fuller; Booth Udall Fuller, PLC (57) ABSTRACT

A topical proprioceptive tube and method of use for at least activating muscle, reducing muscle fatigue, enhancing performance, or reducing a risk of knee injury. The tube includes a flexible sleeve having at least: a hamstring buttress, a knee buttress, or both, wherein the hamstring buttress and the knee buttress are configured to be coupled to the interior of the flexible sleeve such that the hamstring buttress applies pressure to at least a portion of one of the subject's hamstring muscles and the knee buttress applies pressure to at least a portion of the subject's Vastus Medialis Obliquus (VMO) when worn by the subject to provide a desired effect.

20 Claims, 10 Drawing Sheets (51) Int. Cl.
*A61H 1/00* (2006.01)
*A61F 5/30* (2006.01)

(56) References Cited

U.S. PATENT DOCUMENTS 5,267,928 A    12/1993   Barile et al.
5,968,002 A    10/1999   Morrisseau
6,135,974 A    10/2000   Matz
8,845,567 B2 *  9/2014   Herresthal ............ A61F 5/0109
                                               602/26

2005/0154336 A1   7/2005   Kloecker et al.
2005/0261617 A1   11/2005  Hall
2007/0021699 A1   1/2007   Braunstein et al.
2008/0125842 A1   5/2008   Petitt

OTHER PUBLICATIONS

Written Opinion of the International Searching Authority for PCT/US2012/039748 dated Sep. 21, 2012.
International Preliminary Report on Patentability for PCT/US2012/039748 dated May 2, 2013.

* cited by examiner

TOPICAL PROPRIOCEPTIVE ACL TUBE AND METHODS OF USE

RELATED APPLICATIONS

This application is a continuation-in-part application of International Application No. PCT/US2012/039748, titled "Topical Proprioceptive ACL Tube and Methods of Use," filed May 25, 2012, which claims the benefit of U.S. Provisional Application No. 61/490,020, filed May 25, 2011, the contents of each of which are incorporated herein by reference in their entireties.

BACKGROUND OF THE INVENTION

1. Field of the Invention

The present invention relates generally to a medical device designed to enhance performance and reduce the risk of injury to the knee. Comprised of a flexible sleeve with strategically positioned hamstring and knee buttresses, the tube of the present invention is designed to be worn during periods of physical activity or while at rest. In a preferred embodiment, each component of the Tube is composed of resilient, non-rigid material, and the invention increases proprioception and reduces the risk of injury by applying pressure to the hamstring muscles and/or the Vastus Medialis Obliquus ("VMO") of a human subject.

2. Discussion of the Background

Injuries to the Anterior Cruciate Ligament ("ACL") are among the most feared by athletes of any sport. It is estimated that in a single year over a quarter million people will tear their ACL. Roughly 70% of these injuries will require surgical reconstruction at a cost of $17,000 to $25,000 per injury. Indeed, injuries to the ACL are the most common knee ligament injuries. Although the affected individual is able to return to sports in 80-95% of cases, the long-term effects of an ACL tear negatively impact one's quality of life for many years thereafter.

One skilled in the art recognizes that the term "knee" refers to the complex synovial joint in humans that joins the thigh with the leg and consists of two articulations: one between the femur and tibia, and one between the femur and patella. The knee actually comprises three functional compartments: the femoropatellar, or "kneecap", the patellar groove; and the medial and lateral femorotibial articulations linking the femur, or thigh bone, with the tibia, the main bone of the lower leg.

The ACL is one of the four primary ligaments in the human knee (the others being the medial collateral ligament, the posterior cruciate ligament, and the lateral collateral ligament). As used herein, the term "knee injury" refers to a tear, rupture, or other injury to one or more of these ligaments, or to any dislocation, tracking, or other injury to the patella. The ACL extends between the "notch" of the distal femur and the medial wall of the lateral femoral condyle. The two fibrous bundles comprising the ACL are named for where they attach to the tibial plateau: the anteromedial and the posterolateral. The ACL attaches to the (anterior) intercondyloid eminence of the tibia, where it blends with the anterior horn of the lateral meniscus. These attachments provide stability to the knee joint by preventing anterior translation of the tibia in relation to the femur.

Interestingly, ACL tears occur disproportionately among women. Research indicates that women who participate in comparable jumping and cutting athletic activities tear their ACL two-to-nine times more often than their male counterparts. Experts have advanced a number of theories to explain this imbalance, including relative differences in environment, lower limb alignment, muscular strength, jump biomechanics, neuromuscular traits, hormone levels, and fitness level (conditioning). According to one theory, women experience higher rates of ACL tears because their hamstrings and quadriceps contract in a different order and at a different rate than do those of men. When men return to the ground after a vertical jump, their hamstrings generally contract before their quadriceps. This keeps the tibia posterior and protects the ACL from injury. When many women return to the ground after a vertical jump, however, the quadriceps fire first and the knee rotates internally. This physiological response places excessive strain on a woman's knees and may cause injury to her ACL. Thus, knee abduction loading appears to be a critical factor that contributes to the rupture of the ACL. Female athletes generate greater abduction loads when cutting and landing (compared to their male counterparts).

It is therefore hypothesized that knee abduction is a critical factor that contributes to the increased incidence of ACL injuries among women. See, e.g., Palmieri-Smith et. al, "Association of Quadriceps and Hamstrings Cocontraction Patterns with Knee Joint Loading", *Journal of Athletic Training*, 2009; 44(3):256-63. The above study found that women experience lower overall quadriceps-to-hamstrings (Q:H) cocontraction, and that medial-to-lateral Q:H cocontraction appears to be particularly unbalanced in women. This imbalance limits the ability of female athletes to resist abduction loading. This may account for the added incidence of ACL injuries among women, because increased abduction loads create added strain on the ACL. In other words, the experimental and epidemiological evidence suggests that female athletes unwittingly utilize a selective Q:H activation strategy that contributes to abduction loading—a critical factor in the ACL rupture mechanism. Rather than evenly cocontracting the muscles that control abduction loading, women appear to contract the lateral quadriceps and hamstrings while underactivating the medial thigh muscles. Selective activation of the medial knee muscles helps to resist abduction loads. Thus, the pattern of Q:H contraction in women appears harmful to the ACL. In contrast, balanced cocontraction of the quadriceps and hamstrings (in the so-called frontal plane) enhances joint compression, which increases the stability of the knee joint. Overall, the existing research indicates that Q:H cocontraction is lower among female athletes as compared to their male counterparts.

Moreover, women typically have wider hips and a smaller femoral "notch" (to which the proximal end of the ACL attaches). These unique physiological and biomechanical characteristics observed among female athletes often cause greater internal rotation of the knee and result in an increased incidence of ACL injuries. Similarly, increased incidence of issues associated with Patella Femoral subluxation are also believed to occur more frequently in women because of wider hips, which cause the Q angle (the angle between the quadriceps load vector and the patellar tendon load vector) to increase.

Unfortunately, contemporary athletic training programs and orthopedic devices fail to compensate for these unique female characteristics. Existing knee braces and athletic training methods utilize "one-size-fits-all" solutions that all too often focus on men to the exclusion of women. A need exists, therefore, for a device and training method designed to address the unique neurophysiological relationship between the quadriceps, hamstrings, patella, and the ACL in women. Specifically, a need exists for a proprioceptive knee device configured to lower the risk of knee injuries, especially in women athletes. Such a device would preferably enhance neuromuscular communication to coordinate hamstring and quadriceps contraction in women to lower the risk of knee injuries.

SUMMARY OF THE INVENTION

The objective of the present invention is to provide a therapeutic proprioceptive device and method of use for enhancing performance and reducing the risk of knee injury. Instead of a bulky, ill-fitting knee brace commonly used in the art, the present invention comprises a flexible sleeve including an interior surface configured to receive a buttress. An entirety of the interior surface or a continuous and uniform portion of the interior surface is configured to receive the buttress. A hamstring buttress is adjustably coupled to a portion of the interior surface such that a size, orientation, and position of the coupled hamstring buttress are configured to cause the hamstring buttress to cover a portion of one of the subject's hamstring muscles and apply pressure to the portion of one of the subject's hamstring muscles when worn by the subject. A knee buttress is adjustably coupled to a portion of the interior surface such that a size, orientation, and position of the coupled knee buttress are configured to cause the knee buttress to cover a portion of the subject's Vastus Medialis Obliquus (VMO) and apply pressure to the VMO when worn by the subject such that concurrent topical application of pressure by the hamstring buttress and knee buttress reduce an abduction load on the subject's knee.

The present invention is also directed to a therapeutic proprioceptive method for enhancing cocontraction of a human subject's quadriceps and hamstrings, said method comprising the steps of:

(a) applying topical pressure to the subject's hamstring muscles;

(b) applying topical pressure to the subject's Vastus Medialis Obliquus (VMO); and (c) reducing an abduction load on the subject's knee by concurrent topical application of (a) and (b).

The therapeutic proprioceptive method and device of the present invention both prevents injury and aids in the recovery of an injured patient by activating muscles to reduce stress and strain on joints and ligaments through targeted pressure by buttresses within the flexible sleeve. Activation of muscles in effect reduces muscle fatigue and extends joint protection by the activated muscles.

BRIEF DESCRIPTION OF THE DRAWINGS

The accompanying drawings, described below, illustrate preferred embodiments of the present invention. It will be understood that no limitation to the scope of the invention is intended thereby. These drawings depict various features and further advantages of the present invention. The invention is not limited to the particular embodiments disclosed in these drawings, as it should be understood by one skilled in the art that additional features, modifications, and alternative embodiments are contemplated by the invention as disclosed herein.

DETAILED DESCRIPTION OF THE PREFERRED EMBODIMENTS

The following is a description of the preferred embodiments of the present invention and is not intended to limit the scope of the invention to the particular embodiments discussed below.

Figure 1:
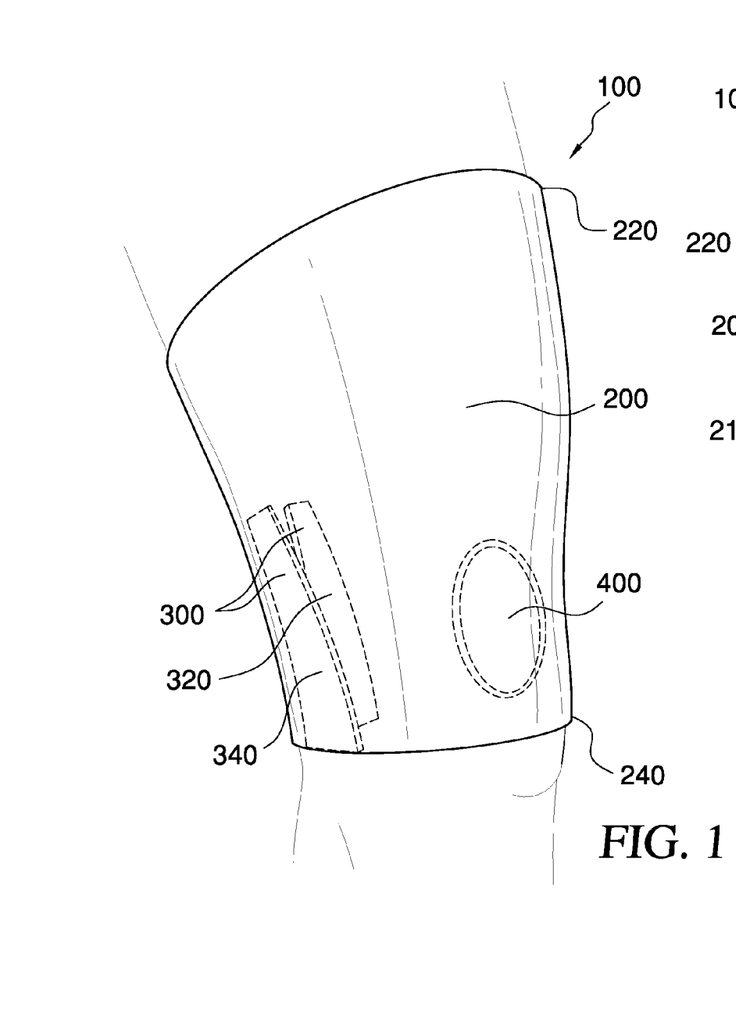
FIG. 1 is a front and side perspective view of a preferred embodiment of the present invention showing the device on a subject's leg.
Figure 2:
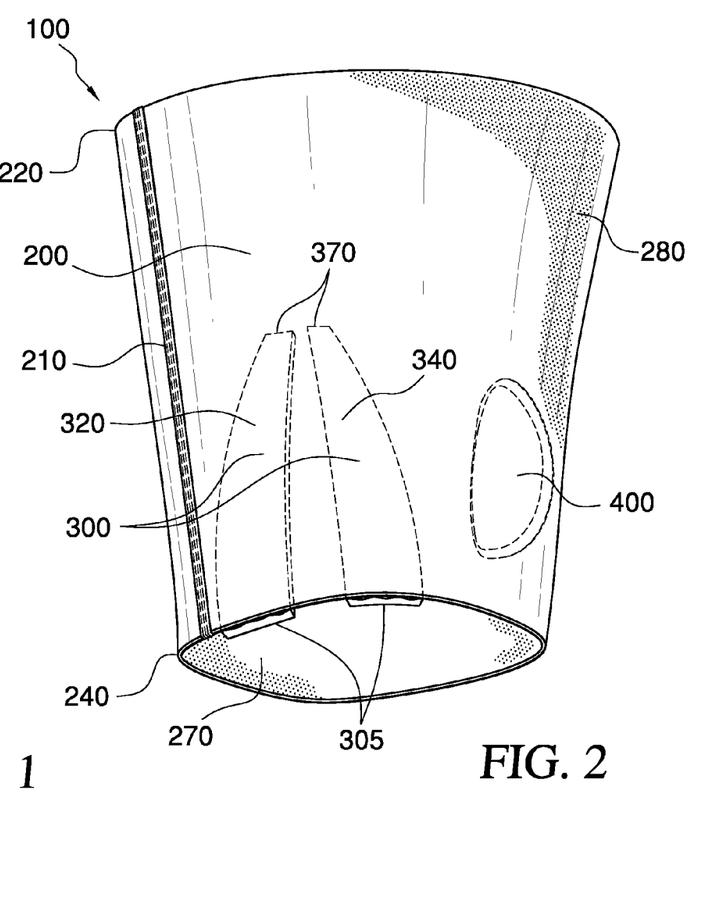
FIG. 2 is a side perspective view of a preferred embodiment of the present invention.
Figure 3:
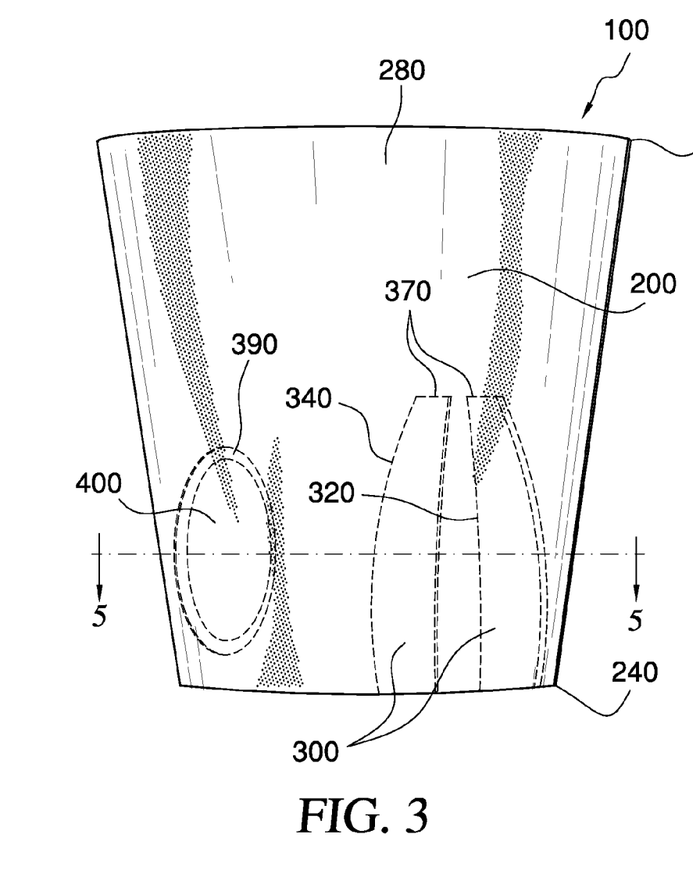
FIG. 3 is a front elevational view of a preferred embodiment of the present invention.
Figure 4:
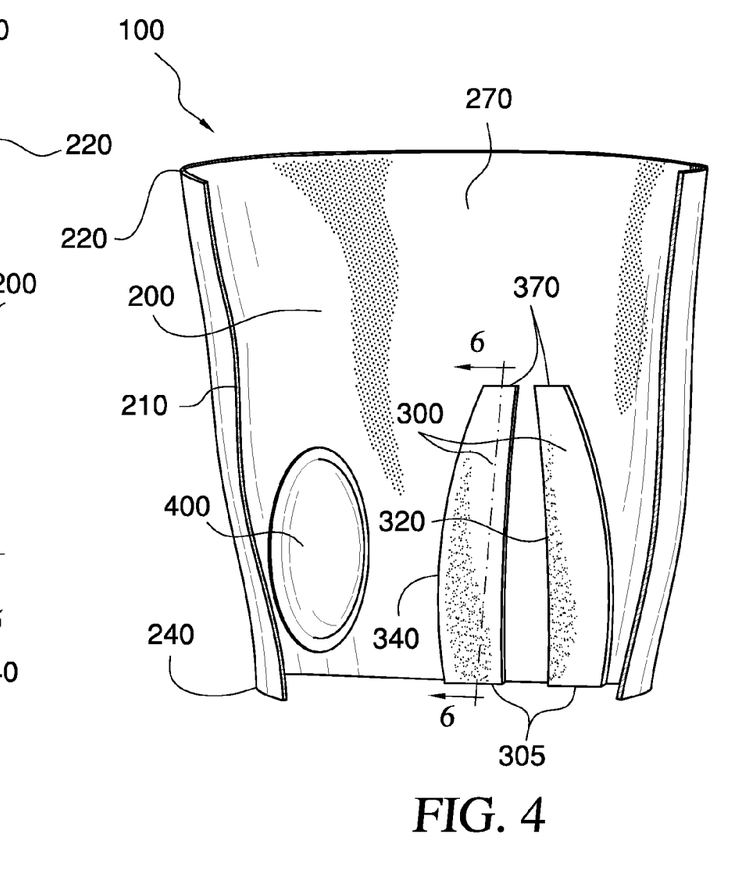
FIG. 4 is an alternate rear elevational view of a preferred embodiment of the present invention.
Figure 5:
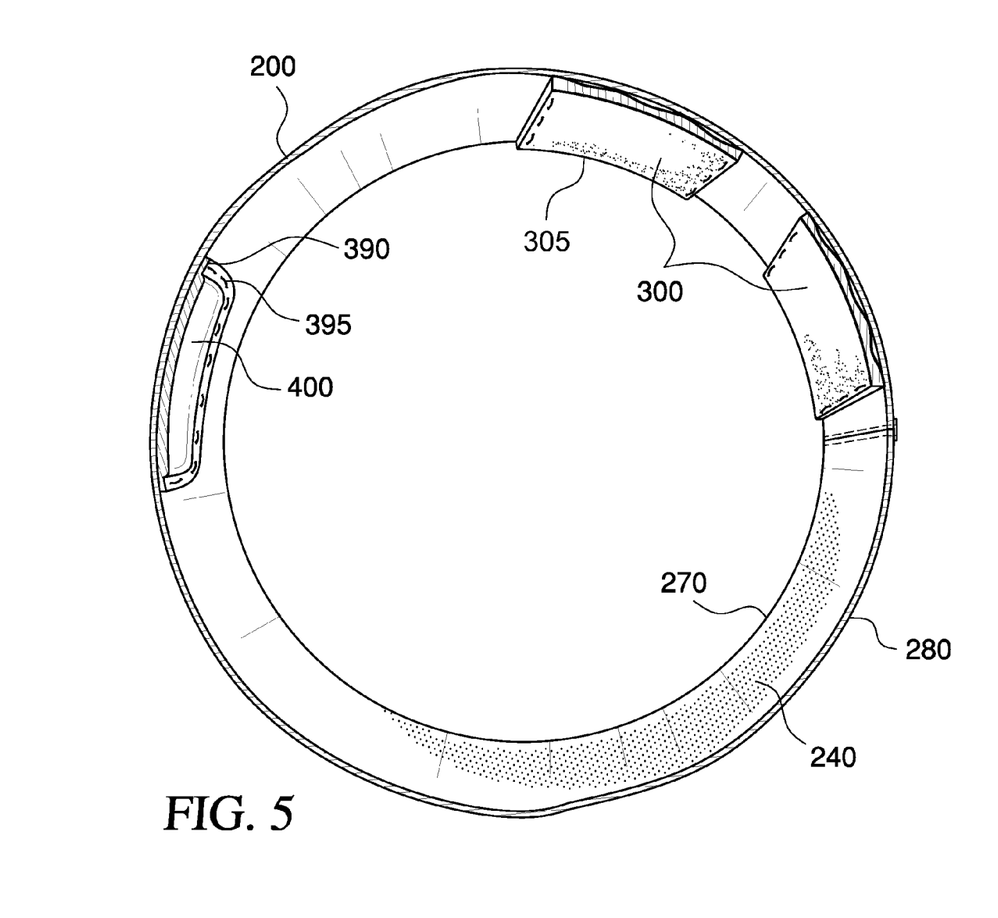
FIG. 5 is a bottom plan view of a preferred embodiment of the present invention.

In accordance with the present invention, FIGS. 1-18 depict topical proprioceptive ACL Tube or topical proprioceptive patella tube 100 for enhancing performance and reducing the risk of knee injuries in human subjects, including women athletes. In a preferred embodiment, topical ACL tube or topical patella tube 100 includes flexible sleeve 200, which is comprised of a lower end 240 and an upper end 220, the upper end 220 and the lower end 240 each having an interior surface 270 and an exterior surface 280. Flexible sleeve 200 is preferably comprised of a thin, resilient, radially stretchable material designed to conform and contour to a subject's knee. Preferably, flexible sleeve 200 is comprised of a loose-knit fiber breathably configured to release perspiration and allow air flow during use. The loose-knit fiber can be any one of a number of commercially available stretchable materials such as LYCRA, SPANDEX, BIOSKIN, or EpX. More preferably, the material is a tri-laminate (bonded) material having a first polyurethancepolyurea copolymer on the inside and a second polyurethane-polyurea copolymer on the outside, with a thin polyurethane membrane between the first and second copolymers. In a preferred embodiment, the tri-laminate material is less than 2 millimeters (mm) thick and is sufficiently elastic to provide between 15-25 mm of pressure in compression to the lower leg, ankle, and/or foot of the subject. As shown in FIGS. 4 and 5, flexible sleeve 200 is stitched together and vertically bisected along seam 210. Optionally, seam 210 is comprised of one or more hook and loop fasteners suitable for releasably coupling the proximal and distal ends of flexible sleeve 200 together along seam 210.

Preferably, the lower (distal) end 240 of flexible sleeve 200 terminates at the superior (top) portion of the patella and the upper (proximal) end 220 terminates approximately between 2.54 centimeters (cm) and 12.7 cm below the gluteal fold. Preferably, upper end 220 of flexible sleeve 200 terminates at least 7.62 cm below the gluteal fold.

In an alternate embodiment, lower end 240 of flexible sleeve 200 extends beyond the patella and terminates in the upper calf region of the lower leg of a subject. Advantageously, this alternative embodiment may include one or more apertures encircling the patella.

Advantageously, topical tube 100 further comprises one or more hamstring buttresses 300. Preferably, as shown in FIGS. 1-12, topical tube 100 includes one or more of: medial hamstring buttress 320, biceps femoris buttress 340, and hamstring buttress 360, wherein medial hamstring buttress 320 biceps femoris buttress 340, and hamstring buttress 360 are coupled to flexible sleeve 200. More specifically, hamstring buttresses 300 are shown coupled to interior surface 270 of the lower end 240 of flexible sleeve 200 and extend into the interior surface 270 of the upper end 220 of flexible sleeve 200. More preferably, when two hamstring buttresses 300 are used, the two hamstring buttresses 300 are mirror images of each other and comprise a lower (distal) base portion 305 and an upper (proximal) portion 370. Most preferably, when two hamstring buttresses 300 are used, the two hamstring buttresses 300 are positioned in the sleeve such that when the topical tube 100 is worn by the subject, both medial hamstring buttress 320 and biceps femoris buttress 340 extend over and apply pressure to the medial hamstring muscles (the semimembranosus and the semitendinosus) and the biceps femoris, respectively. Preferably, medial hamstring buttress 320 is centered over the medial hamstring muscles at approximately 50% of thigh length (measured between the front tip of the hip at the anterior superior iliac spine and the knee joint line). Preferably, the hamstring buttresses 300 are positioned such that the upper (proximal) portion 370 is approximately between 2.54 cm and 14.00 cm below the gluteal fold. More preferably, the upper portion 370 of hamstring buttresses 300 is between 5.08 cm and 10.16 cm below the gluteal fold. Most preferably, hamstring buttresses 300 are positioned such that the upper (proximal) portion is between 7.62 cm and 8.89 cm below the gluteal fold. Alternatively, hamstring buttresses 300, including medial hamstring buttress 320, are positioned such that a center of the buttresses are located a distance in a range of 7.62 cm to 12.70 cm from the break in the back of the knee. Preferably, medial hamstring buttress 320 is positioned with a center of the buttress positioned over the medial hamstrings at distance of approximately 10.16 cm from the break in the back of the knee.

As discussed above, topical tube 100 comprises one or more hamstring buttresses 300. In another preferred embodiment, rather than including a medial hamstring buttress 320 and a separate biceps femoris buttress 340, topical tube 100 includes a single oval, elliptical, or rounded hamstring buttress 360, which is shown, for example, in FIGS. 7-9. Hamstring buttress 360 can also be square, rectangular, or any other shape. Hamstring buttress 360 comprises a lower (distal) base portion 380 and an upper (proximal) portion 385. In an embodiment, hamstring buttress 360 includes a set of opposing parallel sides, shown for example in FIG. 7 as base portion 380 and upper portion 385, and further includes and a set of opposing rounded sides, wherein the rounded sides are connected to the opposing parallel sides. Hamstring buttress 360 is coupled to interior surface 270 towards the lower end 240 of flexible sleeve 200 and extends along interior surface 270 toward upper end 220 of flexible sleeve 200. Hamstring buttress 360 is positioned in the sleeve such that when topical tube 100 is worn by the subject, hamstring buttress 360 extends over and applies pressure to the medial hamstring muscles (the semimembranosus and the semitendinosus) and the biceps femoris. In a preferred embodiment, medial hamstring buttress 360 is centered over the medial hamstring muscles at approximately 50% of thigh length (measured between the front tip of the hip at the anterior superior iliac spine and the knee joint line). Preferably, hamstring buttress 360 is positioned such that the upper (proximal) portion 385 is approximately between 2.54 cm and 14.00 cm below the gluteal fold. Alternatively, the upper portion 385 of hamstring buttress 360 is between 5.08 cm and 10.16 cm or 7.62 cm and 8.89 cm below the gluteal fold. In an embodiment, hamstring buttress 360, is positioned such that a center of the buttress is located a distance in a range of 7.62 cm to 12.70 cm from the break in the back of the knee. More preferably, hamstring buttress 360 is positioned with a center of the buttress positioned over the hamstrings at distance of approximately 10.16 cm from the break in the back of the knee.

In their preferred embodiments, hamstring buttresses 300 are oval shaped, elliptical shaped, or elongated with a set of opposing parallel sides and a set of opposing rounded sides. Preferably, each hamstring buttress 300 is between 2.54 cm and 12.70 cm long. More preferably, hamstring buttresses 300 are between 7.62 cm and 10.16 cm long. Most preferably, hamstring buttresses 300 are 8.57 cm long. In another preferred embodiment, hamstring buttresses 300 are between 6.00 cm and 10.00 cm long. Advantageously, each hamstring buttress 300 is between 2.00 cm and 10.16 cm wide. More advantageously, each hamstring buttress 300 is between 5.08 cm and 7.62 cm wide. Most advantageously, hamstring buttresses 300 are 6.00 cm wide. In another preferred embodiment, hamstring buttresses 300 are between 6.00 cm and 9.00 cm wide. Thus, in their preferred embodiments, hamstring buttresses 300 have a surface area of between 0.82 $cm^2$ and 135.48 $cm^2$. More preferably, hamstring buttresses 300 have a surface area of between 9.75 $cm^2$ and 77.42 $cm^2$.

An amount of pressure applied to the hamstring muscles is determined by a size and material of flexible sleeve 200 as well as by a size and material of hamstring buttresses 300. Advantageously, each hamstring buttress 300 includes a thickness in a range of 0.10 cm to 3.00 cm. More advantageously, each hamstring buttress 300 includes a thickness in a range of 0.25 cm to 1.50 cm. Most advantageously, each hamstring buttress 300 includes a thickness in a range of 0.85 cm to 1.15 cm.

Preferably, the amount of pressure applied to the hamstring muscles by hamstring buttresses 300 is between 15-400 mm Hg of compression. More preferably, the amount of pressure applied to the hamstring muscles by hamstring buttresses 300 is between 25-350 mm Hg of compression. Most preferably, the amount of pressure applied to the hamstring muscles by hamstring buttresses 300 is between 35-200 mm Hg of compression. In another preferred embodiment, the amount of pressure applied to the hamstring muscles by hamstring buttresses 300 is between 30-90 mm Hg of compression.

In a preferred embodiment, hamstring buttress 320 applies more pressure to the medial hamstring muscles than biceps femoris buttress 340 applies to the biceps femoris. In an alternate embodiment, hamstring buttress 320 applies less pressure to the medial hamstring muscles than biceps femoris buttress 340 does to the biceps femoris. In another alternative embodiment, medial hamstring buttress 320 applies the same amount of pressure to the medial hamstring as the biceps femoris buttress 340 applies to the biceps femoris.

In a preferred embodiment, hamstring buttresses 300 are comprised of a compressible material. Preferably, the compressible material is comprised of one or more of the following: foam or foam-like material, a gel or gel-like material, or any other compressible material suitable to apply pressure to the hamstring muscles and receptors. Preferably, flexible sleeve 200 compresses hamstring buttresses 300 toward the subject's hamstrings with a force sufficient to stimulate sensory and tactile receptors located in the hamstring region. Most preferably, hamstring buttresses 300 extend over and apply pressure to the semitendinosus, semimembranosus, biceps femoris, and/or popliteal fossa.

Figure 15:
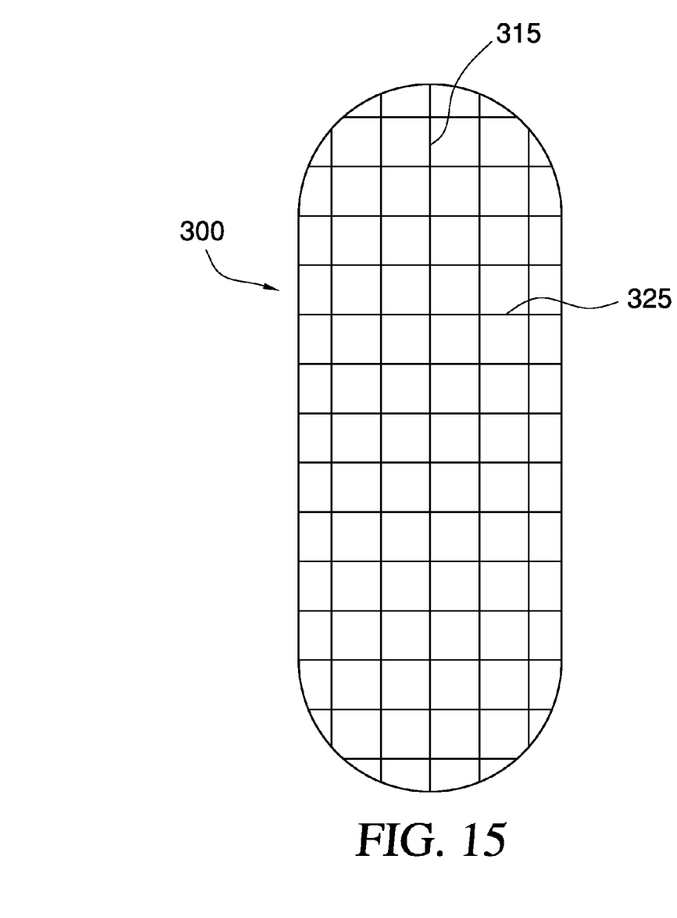
FIG. 15 is a bottom plain view of a preferred embodiment of the present invention showing a grid of rounded lines on an outer surface of a hamstring buttress.
Figure 16:
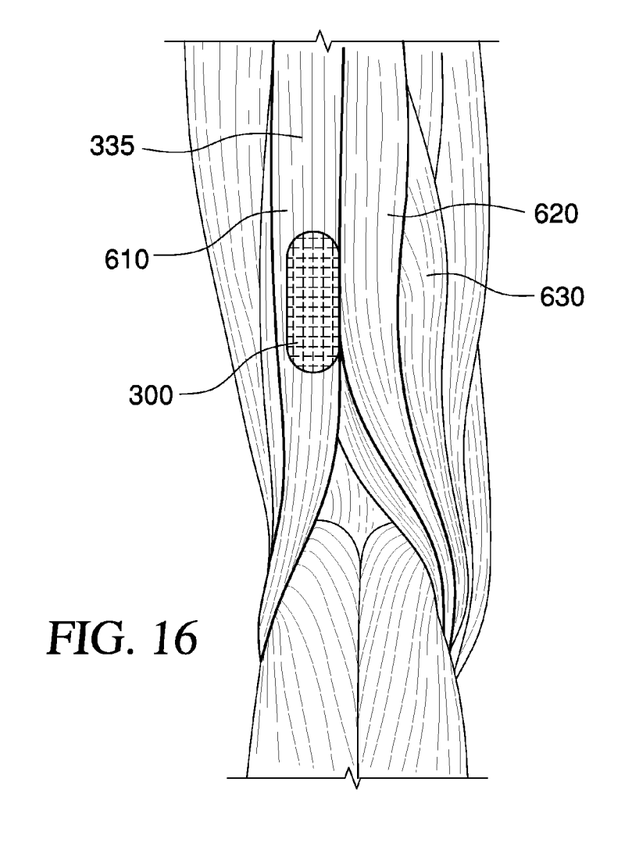
FIG. 16 is a rear elevational view of a leg of a human subject showing a preferred alignment of a hamstring buttress of the present invention.
Figure 17:
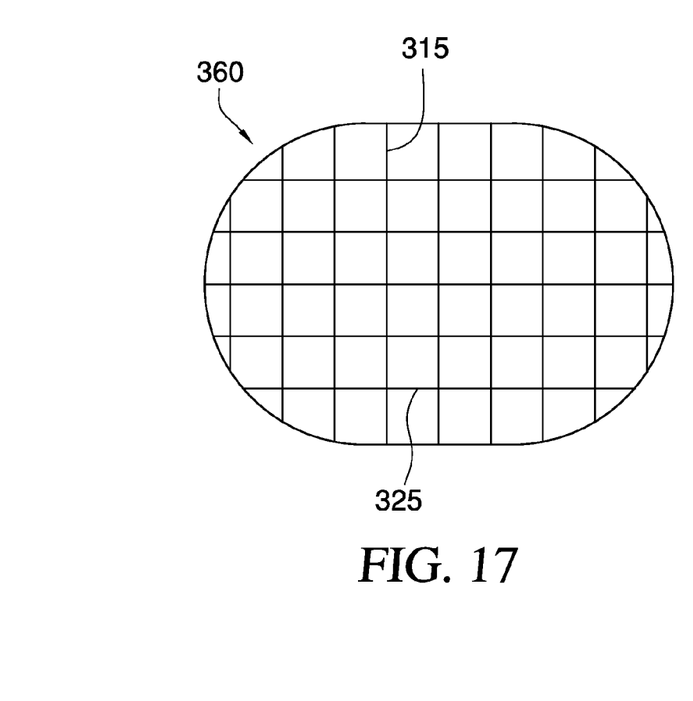
FIG. 17 is a bottom plain view of another preferred embodiment of the present invention showing a grid of rounded lines on an outer surface of a hamstring buttress.
Figure 18:
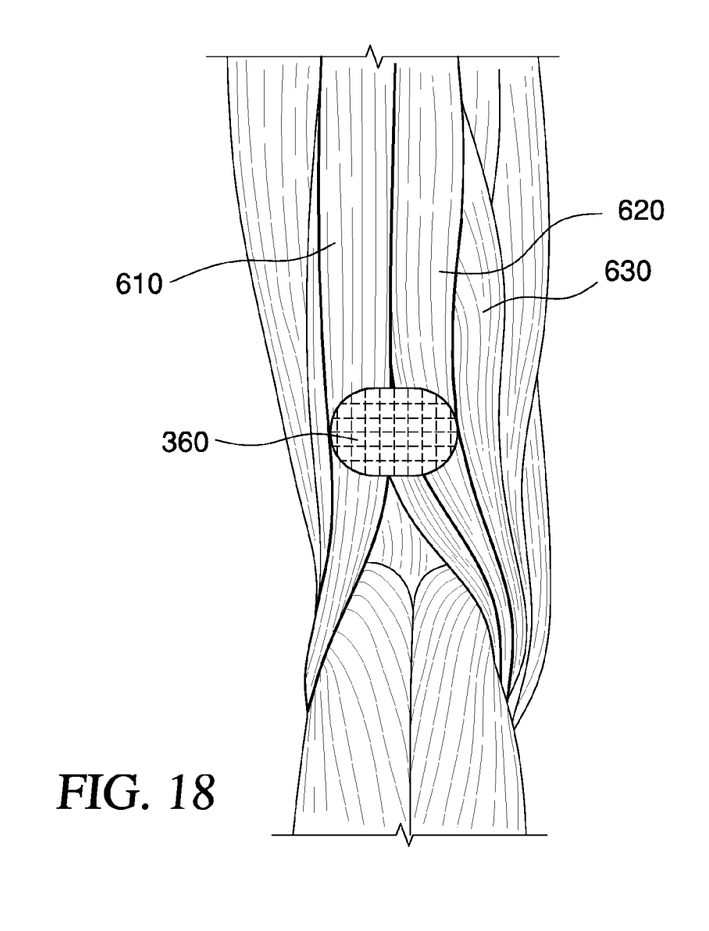
FIG. 18 is a rear elevational view of a leg of a human subject showing another preferred alignment of a hamstring buttress of the present invention.

Advantageously, hamstring buttresses 300 are solid and are formed as continuous structures without openings or voids that extend completely through the buttresses. Preferably, hamstring buttresses 300 further comprise two sets of grid lines 315 and 325 on the outer surface of medial hamstring buttress 320, biceps femoris buttress 340, and hamstring buttress 360. Preferably, grid lines 315 and 325 extend partially but not completely through hamstring buttresses 300. More preferably, the first set of grid lines 315 are oriented or run parallel to the medial hamstring muscle fibers 335. The second set of grid lines 325 are oriented differently than the first set of grid lines 315 and can run perpendicular to the first set of grid lines 315 or the medial hamstring muscle fibers 335. Preferably, each rounded grid line 315, 325 is between 0.16 cm and 1.27 cm wide and between 0.32 cm and 2.54 cm deep. More preferably, each rounded grid line 315 and 325 is between 0.32 cm and 0.64 cm wide and between 0.64 cm and 1.28 cm deep (perpendicular lines may be deeper in order to enhance proprioception). The preferred rounded grid lines 315 and 325 are typically grooves formed below the horizon of the hamstring buttress's outer surface. Alternatively, however, grid lines 315 and 325 can also rise above the surface of the hamstring buttresses and provide the required effect.

Figure 6:
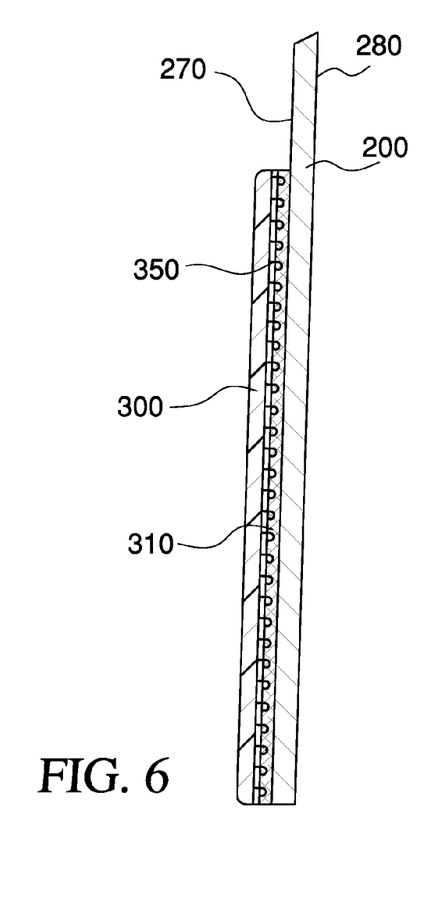
FIG. 6 is a cross-sectional view of a preferred embodiment of the present invention showing a hamstring buttress optionally attached via hook and loop fasteners.
Figure 7:
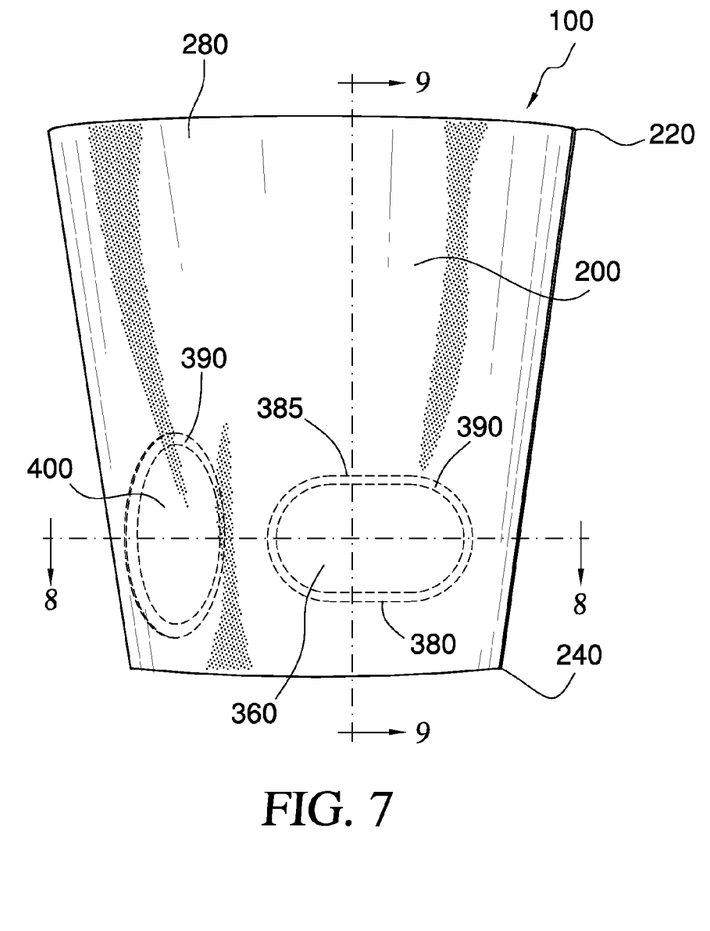
FIG. 7 is a front elevational view of another preferred embodiment of the present invention.
Figure 8:
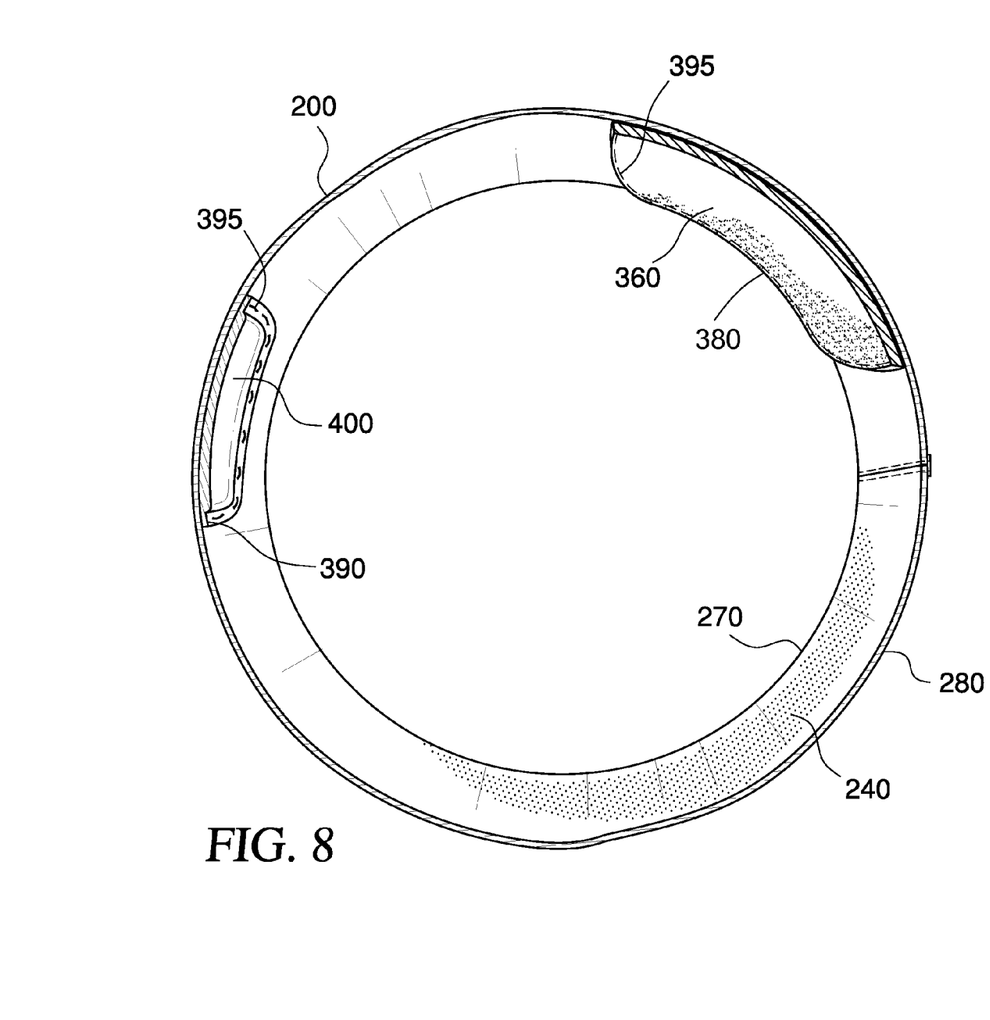
FIG. 8 is a bottom plan view of another preferred embodiment of the present invention.
Figure 9:
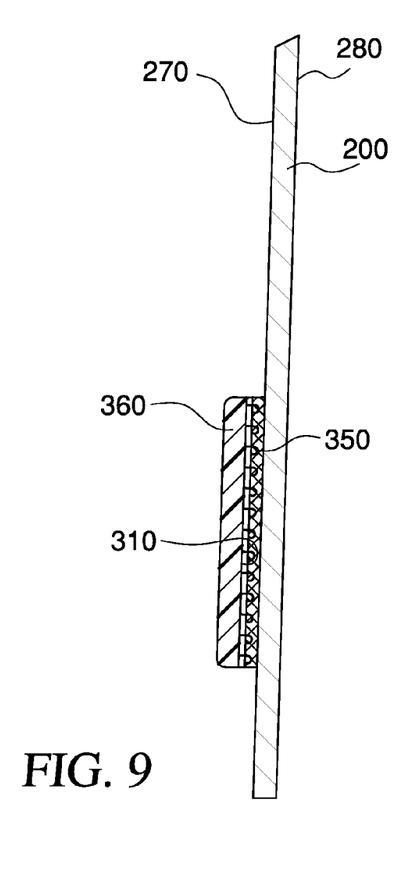
FIG. 9 is a cross-sectional view of another preferred embodiment of the present invention showing a hamstring buttress optionally attached via hook and loop fasteners.
Figure 10:
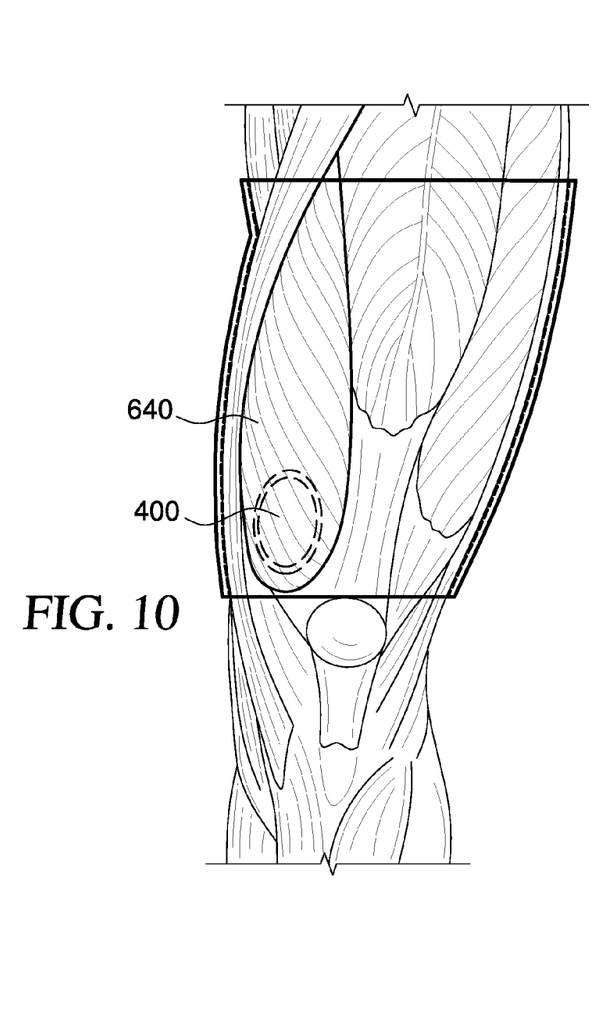
FIG. 10 is a front elevational view of a preferred embodiment of the present invention showing the device on the leg of a human subject.
Figure 11:
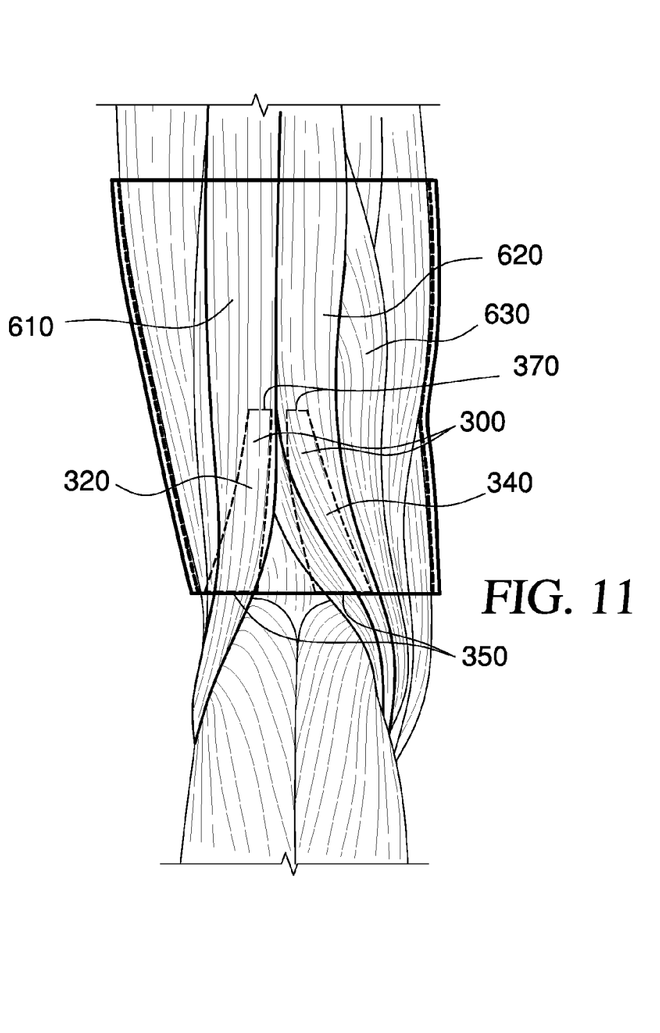
FIG. 11 is a rear elevational view of a preferred embodiment of the present invention showing the device on the leg of a human subject.
Figure 12:
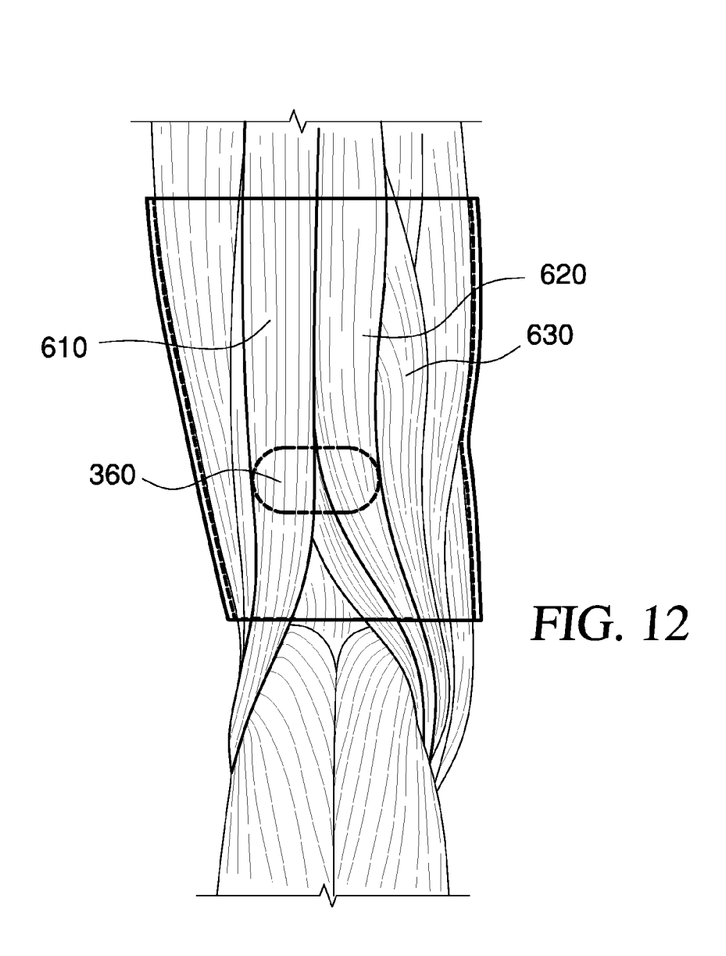
FIG. 12 is a rear elevational view of another preferred embodiment of the present invention showing the device on the leg of a human subject.

Preferably, hamstring buttresses 300 are releasably coupled to the interior of flexible sleeve 200. More preferably, hamstring buttresses 300 are further comprised of hook and loop fasteners 350 affixed to the interior portion 310 of the hamstring buttresses 300, wherein the hook and loop fasteners are suitable for releasably coupling the interior portion 310 of hamstring buttresses 300 to the interior surface 270 of flexible sleeve 200. More preferably, both hamstring buttress 320 and biceps femoris buttress 340 are releasably coupled to the interior surface 270 of the lower end 240 of flexible sleeve 200. Most preferably, hamstring buttress 360 is releasably coupled to the interior surface 270 of the lower end 240 of flexible sleeve 200.

In another preferred embodiment, hamstring buttresses 300 are fixedly or permanently coupled to flexible sleeve 200. Preferably, hamstring buttresses 300 are affixed to the interior surface 270 of flexible sleeve 200 using stitching, knitting, or a thickening weave 395. Alternatively, hamstring buttresses 300 are disposed within flexible sleeve 200. For example, hamstring buttresses 300 can be disposed between layers of material comprising flexible sleeve 200, or can be incorporated within the flexible sleeve, such as being incorporated within a knit sleeve. Stitching 395 is formed using thread, line, or other suitable material that passes through hamstring buttresses 300 and through flexible sleeve 200. Tension is applied to stitching 395 to draw or hold hamstring buttresses 300 and flexible sleeve 200 fixedly together. Preferably, stitching 395 is formed at a peripheral area or near an edge of hamstring buttresses 300. Alternatively, stitching 395 is formed over any portion of hamstring buttresses 300 and can cover an entirety of the hamstring buttresses. In an embodiment, stitching 395 is formed in or along flange or tapered portion 390. Flange 390 may be formed at a peripheral area or at an edge of hamstring buttresses 300 and can include a thickness less than a thickness of a center portion of hamstring buttresses 300.

Advantageously, topical tube 100 further comprises one or more knee buttresses 400 coupled to the interior surface 270 of the lower end 240 of flexible sleeve 200. Preferably, the one or more knee buttresses 400 comprise an oval shape, an elliptical shape, or an elongated shape including a set of opposing parallel sides and a set of opposing rounded sides connected to the opposing parallel sides. Knee buttress 400 can be formed of resilient material, wherein the knee buttress 400 is configured to extend at least partially over and apply pressure to the subject's VMO. Preferably, knee buttress 400 is centered over the medial hamstring muscles at approximately 67% of thigh length (measured between the front tip of the hip at the anterior superior iliac spine and the knee joint line). Advantageously, knee buttress 400 is between 2.54 cm and 7.62 cm wide and 5.00 cm and 10.16 cm long. More advantageously, knee buttress 400 is between 4.00 cm and 6.00 cm wide and between 5.00 cm and 9.00 cm long. Most advantageously, knee buttress 400 is 6.00 cm wide and 8.57 cm long. In a preferred embodiment, the surface area of the knee buttress 400 is between 0.10 cm$^2$ and 135.48 cm$^2$. More preferably, the surface area of knee buttress 400 is between 7.62 cm$^2$ and 67.74 cm$^2$. In a preferred embodiment, the distal end of buttress 400 terminates 1.27 cm to 5.08 cm above the patella. More preferably, the distal end of buttress 400 terminates 2.54 cm to 3.81 cm above the patella. In another preferred embodiment, the distal end of buttress 400 is disposed between 0.50 cm and 5.00 cm above the attachment of the VMO to bone when flexible sleeve 200 is worn by the subject. Preferably, knee buttress 400 is disposed between 1.27 cm and 3.81 cm above the attachment of the VMO to bone when flexible sleeve 200 is worn by the subject. More preferably, knee buttress 400 is disposed 2.54 cm above the attachment of the VMO to bone when flexible sleeve 200 is worn by the subject.

An amount of pressure applied to the VMO is determined by a size and material of flexible sleeve 200 as well as by a size and material of knee buttress 400. Advantageously, knee buttress 400 includes a thickness in a range of 0.10 cm to 3.00 cm. More advantageously, knee buttress 400 includes a thickness in a range of 0.25 cm to 1.50 cm. Most advantageously, knee buttress 400 includes a thickness in a range of 0.85 cm to 1.15 cm.

Preferably, the amount of pressure applied to the VMO is between 15-400 mm Hg of compression. More preferably, the amount of pressure applied to the VMO by knee buttress 400 is between 25-350 mm Hg of compression. Most preferably, the amount of pressure applied to the VMO by knee buttress 400 is between 35-200 mm Hg of compression. In another preferred embodiment, the amount of pressure applied to the hamstring muscles by hamstring buttresses 300 is between 30-90 mm Hg of compression.

In a preferred embodiment, knee buttress 400 is comprised of a compressible material. Preferably, the compressible material is comprised of one or more of the following: foam or foam-like material, a gel or gel-like material, or any other compressible material suitable to apply pressure to the VMO muscle and receptors. Preferably, flexible sleeve 200 compresses knee buttress 400 towards the subject's VMO with a force sufficient to stimulate sensory and tactile receptors located in the subject's VMO.

Figure 13:
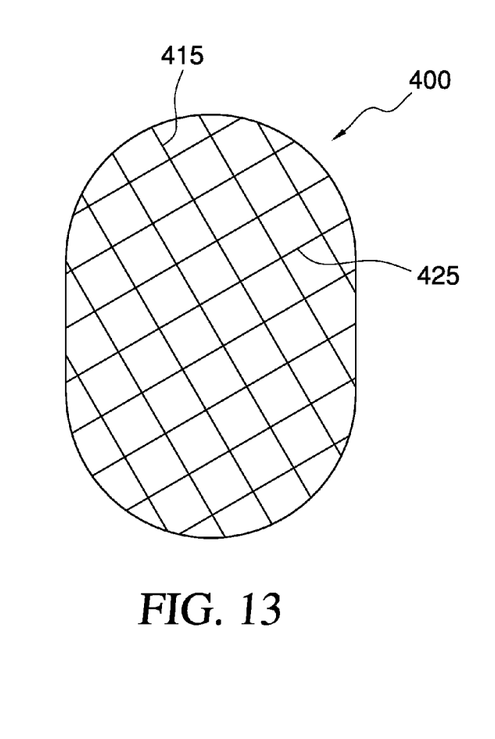
FIG. 13 is a bottom plain view of a preferred embodiment of the present invention showing a grid of rounded lines on an outer surface of a knee buttress.
Figure 14:
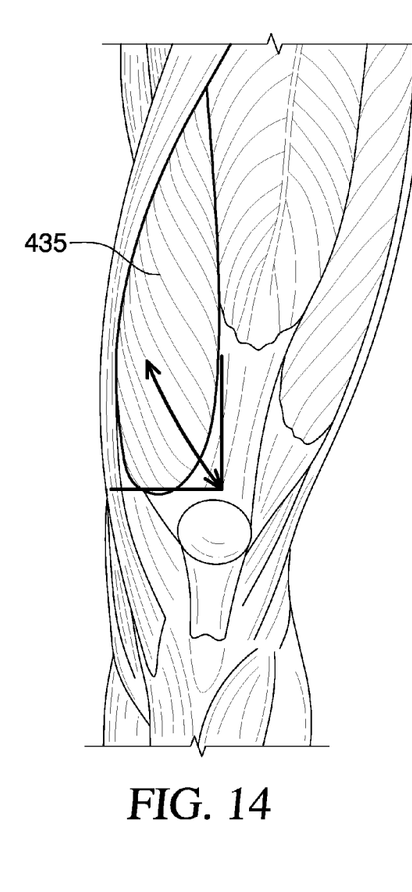
FIG. 14 is a front elevational view of a leg of a human subject showing a preferred alignment of a knee buttress of the present invention.

Advantageously, knee buttress 400 is solid and formed as a continuous structure without openings or voids that extend completely through the buttress. Preferably, knee buttress 400 further comprises two sets of grid lines 415 and 425 on the outer surface 405 of knee buttress 400. Preferably, grid lines 415 and 425 extend partially but not completely through knee buttress 400. More preferably, the first set of grid lines 415 run parallel to the VMO muscle fibers 435 and the second set of grid lines 425 run perpendicular to the VMO muscle fibers 435. The first set of grid lines preferably run parallel to the VMO muscle fibers 435 and are positioned at a 60 degree angle on the outer surface 405 of the knee buttress 400 to provide the desired effect. Furthermore, each grid line 415 and 425, preferably rounded, is between 0.32 cm and 0.64 cm wide and between 0.64 and 1.27 cm deep (perpendicular lines may be deeper in order to enhance proprioception). The preferred rounded grid lines are typically grooves formed below the horizon of the knee buttress's outer surface. Alternatively, however, the grid lines 415 and 425 can also rise above the surface of the knee buttress and provide the required effect.

Preferably, knee buttress 400 is releasably coupled to the interior of flexible sleeve 200. More preferably, knee buttress 400 is further comprised of hook and loop fasteners affixed to an interior portion of knee buttress 400, wherein the hook and loop fasteners are suitable for releasably coupling the interior portion of knee buttress 400 to the interior surface 270 of flexible sleeve 200. Most preferably, knee buttress 400 is releasably coupled to the interior surface 270 of the lower end 240 of flexible sleeve 200 such that when flexible sleeve 200 is worn by the subject, knee buttress 400 is disposed over the subject's VMO.

In another preferred embodiment, knee buttress 400 is fixedly or permanently coupled to flexible sleeve 200. Preferably, knee buttress 400 is affixed to the interior surface 270 of flexible sleeve 200 using stitching, knitting, or a thickening weave 395. Alternatively, knee buttress 400 is disposed within flexible sleeve 200. For example, knee buttress 400 can be disposed between layers of material comprising flexible sleeve 200, or can be incorporated within the flexible sleeve, such as being incorporated within a knit sleeve. Stitching 395 is formed using thread, line, or other suitable material that passes through knee buttress 400 and through flexible sleeve 200. Tension is applied to stitching 395 to draw or hold knee buttress 400 and flexible sleeve 200 fixedly together. Preferably, stitching 395 is formed at a peripheral area or near an edge of knee buttress 400. Alternatively, stitching 395 is formed over any portion of knee buttress 400 and can cover an entirety of the knee buttress. In an embodiment, stitching 395 is formed in or along flange or tapered portion 390. Flange 390 may be formed at a peripheral area or at an edge of knee buttress 400 and include a thickness less than a thickness of a center portion of knee buttress 400.

In a preferred embodiment, tube 100 comprises medial hamstring buttress 320, biceps femoris buttress 340, and knee buttress 400. Preferably, tube 100 is positioned on the leg and/or knee of the subject such that that medial hamstring buttress 320 and the biceps femoris buttress 340 extend substantially over and apply pressure to the hamstring muscles or a belly of the hamstring muscles (the semimembranosus, semitendinosus, biceps femoris, and/or popliteal fossa) and knee buttress 400 extends substantially over and applies pressure to the VMO. More preferably, the tube 100 is positioned such that: buttress 320 extends substantially over and applies pressure to the medial hamstring muscles, biceps femoris buttress 340 extends substantially over and applies pressure to the biceps femoris, and knee buttress 400 extends substantially over and applies pressure to the VMO. Advantageously, hamstring buttress 320 mirrors the medial hamstring musculature, biceps femoris buttress 340 mirrors the biceps femoris musculature, and knee buttress 400 mirrors the shape of the VMO. In alternate embodiments, hamstring buttress 320 and biceps femoris buttress 340 include a tapered base portion 305 and a wide upper portion 370. Alternatively, medial hamstring buttress 320 and biceps femoris buttress 340 include a wide base portion 305 and a tapered upper portion 370.

In an alternate embodiment, hamstring buttress 320 substantially covers (e.g., at least 50%, 60%, 70%, 80% or 90%) and applies pressure to the medial hamstring muscles but preferably does not substantially extend over, or apply pressure to, any other part of the leg or knee covered by flexible sleeve 200. In this embodiment, biceps femoris buttress 340 substantially covers and applies pressure to the semimembranosus and semitendinosus but preferably does not substantially extend over other parts of the leg or knee covered by flexible sleeve 200. In this same embodiment, knee buttress 400 substantially covers and applies pressure to the VMO or a belly of the VMO but does not extend over or apply pressure to any other part of the leg or knee covered by flexible sleeve 200.

In another preferred embodiment, hamstring buttress 320 is positioned such that it substantially covers and applies pressure to the medial hamstring musculature without radially extending into, extending over, or intruding upon any other hamstring muscles or any ancillary portion of flexible sleeve 200. In this most preferred embodiment, biceps femoris buttress 340 substantially covers and applies pressure to the biceps femoris without radially extending into, extending over, or intruding upon the medial hamstring muscles or any ancillary portion of flexible sleeve 200. In this same preferred embodiment, knee buttress 400 substantially covers and applies pressure to the VMO but does not radially extend into, extend over, or intrude upon the medial or lateral hamstring muscles or any ancillary portion of flexible sleeve 200. In this preferred form, tube 100 and flexible sleeve 200 are positioned such that biceps femoris buttress 340, hamstring buttress 320, and knee buttress 400 are each positioned as described hereinabove.

In another most preferred embodiment, tube 100 comprises only two buttresses affixed and/or releasably coupled to flexible sleeve 200. The two buttresses affixed to tube 100 can be hamstring buttress 360 and knee buttress 400. Additionally, hamstring buttress 360 can include a size similar to or equal to a size of hamstring buttress 360. Alternatively, hamstring buttress 360 includes a width greater than or less than a width of knee buttress 400. In another embodiment, the two buttresses affixed to tube 100 can be medial hamstring buttress 320 and knee buttress 400. Advantageously, knee buttress 400 applies more pressure to the VMO than hamstring buttresses 300 apply to the hamstring muscles. In an alternate embodiment, knee buttress 400 applies less pressure to the VMO than hamstring buttresses 300 apply to the hamstring muscles. In another alternative embodiment, knee buttress 400 applies the same amount of pressure to the VMO as the hamstring buttresses 300 apply to the hamstring muscles.

In yet another most preferred embodiment, tube 100 comprises only one knee buttress 400 affixed and/or releasably coupled to flexible sleeve 200. Topical pressure delivered to a patient's VMO by knee buttress 400, when disposed within flexible sleeve 200 and worn by the patient, has been found to activate, engage, stimulate, "fire," or strengthen the VMO and reduce pain, muscle fatigue, and discomfort of the patient. By engaging the VMO with tube 100, the VMO can help stabilize the knee by balancing or counteracting forces applied to the patella, including tension applied to the patella by the Vastus Lateralis. By activating the VMO with tube 100, a patient's patella can track properly while pain and discomfort experienced as a result of unbalanced loading on the knee can also be reduced. The activated VMO also reduces a risk of injury to the knee by reducing muscle fatigue, which in turn, reduces stress and strain on the knee and ligaments of the knee.

A method of using tube 100, especially during injury recovery, includes patients wearing the tube for a minimum amount of time each day during a set period. Preferably, tube 100 is worn for at least half an hour a day for approximately 1-6 weeks. More preferably, tube 100 is worn for at least an hour a day for 15-30 days. Most preferably, tube 100 is worn at least 2 hours a day for approximately 30 days. Additionally, tube 100 can also be worn for periods of exercise and training Alternatively, tube 100 is worn as needed, for example, during periods of increased activity, during athletic events such as competitions, training, or conditioning, and at times when pain or irritation occurs.

A method of using tube 100, especially during injury prevention, includes wearing tube 100 during periods of increased physical activity and during periods in which muscles experience fatigue. Muscle fatigue often reduces protection offered to a joint by the surrounding muscle, increasing stress and strain on the joint and ligaments of the joint. For example, athletes that tear ligaments are often injured late in a game or athletic competition because fatigued muscles are no longer sufficiently activated to protect ligaments. Patients can reduce a risk of injury by applying topical proprioceptive pressure to specific muscles by wearing tube 100 with one or more properly placed buttress, such as buttresses 300 or 400, which activate targeted muscles. Activation of targeted muscles can slow a process of muscle fatigue and increase activity of a fatigued muscle. By activating fatigued muscles, activated muscles provide greater protection for longer periods of time for joint structures, including ligaments, thereby effectively extending joint protection and reducing a risk of injury.

Advantageously, a portion or an entirety of interior surface 270 of flexible sleeve 200 can be a continuous and uniform surface configured to receive knee buttress 400 or any one or more hamstring buttresses 300. Knee buttress 400 or any one or more hamstring buttresses 300 can be releasably or fixedly attached to interior surface 270. By configuring a portion or an entirety of interior surface 270 to receive buttresses 300 and 400, a size, orientation, and location of the buttresses can be adjusted on flexible sleeve 200 to respond to individual patient needs, such as reducing an abduction load on the subject's knee to reduce a risk of the subject injuring an anterior cruciate ligament or reducing patella femoral sublaxation. Knee buttress 400 or any one or more hamstring buttresses 300 are not limited to specific sizes or orientations because of flexible sleeve 200. Similarly, buttresses 300 and 400 are not limited to being attached at a discrete number of predetermined positions because of flexible sleeve 200. Furthermore, by adjustably positioning buttresses 300 and 400 on interior surface 270, a position of the buttresses can be located on interior surface 270 so as to be disposed over, and apply pressure to, a particular subject's muscles when flexible sleeve 200 is worn by the subject. Thus, the adjustable positioning of buttresses 300 and 400 allows for customization of buttress location within the flexible sleeve based on an individual subject's, size, condition, or need. Similarly, a size of buttresses 300 and 400 can be adjusted based on an individual subject's size, condition, or need, to apply a desired amount of pressure at a desired location on a desired portion of an individual subject's muscles.

In another alternate embodiment, tube 100 of the present invention is included in a topical proprioceptive ACL tube kit. The kit includes, separately, flexible sleeve 200, one or more hamstring buttresses 300, and one or more knee buttresses 400. Preferably, the kit includes printed instructions relating to the use of the topical tube 100, including instructions to couple hamstring buttresses 300 to interior surface 270 of lower end 240 of flexible sleeve 200 such that hamstring buttresses 300 extend into the interior surface 270 of the upper end 220. More preferably, the printed instructions explain that hamstring buttresses 300 should be situated such that they extend over and apply pressure to the hamstring muscles as set forth above. Most preferably, the printed instructions explain that hamstring buttresses 300 should be situated such that they extend over and apply pressure to the semitendinosus 630, semimembranosus 620, biceps femorus 610, and/or popliteal fossa of the subject. Advantageously, the printed instructions further include instructions for coupling the one or more knee buttresses 400 to interior surface 270 of the lower end 240 of flexible sleeve 200. Preferably, the printed instructions include specific instructions relating to the positioning of knee buttress 400 such that it extends at least partially over and applies pressure to the subject's VMO 640.

The present invention also comprises methods of using the topical proprioceptive tube 100 of the present invention for enhancing an athlete's performance and/or reducing the risk of a knee and/or hamstring injury. A method comprises (1) applying the topical ACL tube of the present invention to the subject's knee (2) during physical activities (3) over an interval of time. Preferably, the injury prevented is an injury to the ACL.

In another alternative embodiment or embodiments, the above device is optionally configured to supply transcutaneous nerve stimulation (TENS), heat, and/or cold to subject-selected regions along or between upper end 220 and/or lower end 240.

Upon reading the teachings of this specification, those with ordinary skill in the art will appreciate that, under certain circumstances, considering issues such as changes in technology, subject requirements, etc., a variety of fastening devices may be used to "attach," "fasten," "secure", "releasably secure", and/or "releasably couple" one or more components of the present invention. These fasteners or fastening means may include one or more of the following:

adhesives, bolts, buckles, clasps, latches, locks, screws, snaps, clamps, connectors, couplings, ties or other fastening means yet to be developed.

Likewise, upon reading the teachings of this specification, those with ordinary skill in the art will appreciate that, under certain circumstances, considering issues such as changes in technology, subject requirements, etc., a variety of fastening devices, such as adhesives, belts, bolts, buckles, clasps, latches, locks, screws, snaps, clamps, connectors, couplings, ties or other fastening means yet to be developed may be used in lieu of—or in conjunction with—any of the fasteners or fastening means discussed above.

Although applicant has described applicant's preferred embodiments of this invention, it will be understood that the broadest scope of this invention includes modifications. Such scope is limited only by the claims as read in connection with the above specification. Further, many other advantages of applicant's invention will be apparent to those skilled in the art from the above descriptions and the claims below.

I claim:

1. A topical proprioceptive tube for a human subject, comprising:
   a flexible sleeve including an interior surface configured to receive a buttress, wherein the topical proprioceptive tube comprises no more than two buttresses;
   a first buttress comprising a hamstring buttress adjustably coupled to a portion of the interior surface such that a size, orientation, and position of the coupled hamstring buttress are configured to cause the hamstring buttress to cover a portion of one of the subject's hamstring muscles and apply pressure to the portion of one of the subject's hamstring muscles when worn by the subject, wherein the hamstring buttress is configured to extend over and apply pressure to a belly of at least one of the semitendinosus, semimembranosus, biceps femoris, or popliteal fossa without substantially extending over or applying pressure to any other part of the subject's leg or knee covered by the flexible sleeve; and
   a second buttress comprising a knee buttress adjustably coupled to a portion of the interior surface such that a size, orientation, and position of the coupled knee buttress are configured to cause the knee buttress to cover a portion of the subject's Vastus Medialis Obliquus (VMO) and apply pressure to the VMO when worn by the subject such that concurrent topical application of pressure by the hamstring buttress and the knee buttress reduce an abduction load on the subject's knee, wherein the knee buttress is configured to extend over and apply pressure to a belly of the VMO and activate the VMO without extending over the Vastus Lateralis and without substantially extending over or applying pressure to any other part of the subject's leg or knee covered by the flexible sleeve.

2. The topical proprioceptive tube of claim 1, wherein the buttresses are configured to apply between 15-90 millimeters Hg of pressure to the subject's muscle.

3. The topical proprioceptive tube of claim 1, wherein the hamstring buttress includes a shape similar to a shape of the knee buttress.

4. The topical proprioceptive tube of claim 1, wherein the knee buttress and the hamstring buttress are between 4.0 centimeters (cm) and 6.0 cm wide and between 5.0 cm and 9.0 cm long.

5. The topical proprioceptive tube of claim 1, wherein a continuous and uniform portion of the interior surface is configured to receive a buttress.

6. The topical proprioceptive tube of claim 1, wherein a center of the hamstring buttress is configured to be disposed a distance of 7.62 to 12.7 centimeters from a break in a back of the subject's knee.

7. The topical proprioceptive tube of claim 1, wherein the size, orientation, and position of the hamstring buttress and the knee buttress are configured to concurrently apply topical pressure that reduces an abduction load on the subject's knee and reduces a risk of the subject injuring an anterior cruciate ligament or reduces patella femoral sublaxation.

8. The topical proprioceptive tube of claim 1, wherein a center of the hamstring buttress is configured to be disposed a distance of approximately 50% of the length of the subject's thigh; and a center of the knee buttress is disposed a distance of approximately 67% of the length of the subject's thigh.

9. A topical proprioceptive tube for a human subject, comprising:
   a flexible sleeve including an interior surface configured to receive a buttress, wherein the topical proprioceptive tube comprises no more than two buttresses;
   a first buttress comprising a hamstring buttress adjustably coupled to a portion of the interior surface such that orientation and position of the coupled hamstring buttress are configured to cause the hamstring buttress to apply pressure to the subject's hamstring muscles, wherein the hamstring buttress is configured to extend over and apply pressure to a belly of at least one of the semitendinosus, semimembranosus, biceps femoris, or popliteal fossa without substantially extending over or applying pressure to any other part of the subject's leg or knee covered by the flexible sleeve; and
   a second buttress comprising a knee buttress adjustably coupled to a portion of the interior surface such that an orientation and position of the coupled knee buttress are configured to cause the knee buttress to apply pressure to the Vastus Medialis Obliquus (VMO) when worn by the subject such that concurrent topical application of pressure by the hamstring buttress and the knee buttress reduce a load on the subject's knee, wherein the knee buttress is configured to extend over and apply pressure to a belly of the VMO and activate the VMO without extending over the Vastus Lateralis and without substantially extending over or applying pressure to any other part of the subject's leg or knee covered by the flexible sleeve.

10. The topical proprioceptive tube of claim 9, wherein the hamstring buttress and the knee buttress are formed as solid continuous structures formed of resilient or compressible material.

11. The topical proprioceptive tube of claim 9, wherein the hamstring buttress and the knee buttress are configured to apply between 15-90 millimeters Hg of pressure to the subject's muscle.

12. The topical proprioceptive tube of claim 9, wherein the hamstring buttress includes a shape similar to a shape of the knee buttress.

13. The topical proprioceptive tube of claim 9, wherein the knee buttress and the hamstring buttress are between 4.0 centimeters (cm) and 6.0 cm wide and between 5.0 cm and 9.0 cm long.

14. The topical proprioceptive tube of claim 9, wherein the orientation and position of the hamstring buttress and the knee buttress are configured to concurrently apply topical pressure that reduces an abduction load on the subject's knee and reduces a risk of the subject injuring an anterior cruciate ligament or reduces patella femoral sublaxation.

15. The topical proprioceptive tube of claim 9, wherein a center of the hamstring buttress is configured to be disposed a distance of approximately 50% of the length of the subject's thigh; and a center of the knee buttress is disposed a distance of approximately 67% of the length of the subject's thigh.

16. A topical proprioceptive tube for a human subject, comprising:
a flexible sleeve including an interior surface configured to receive a buttress, wherein the topical proprioceptive tube comprises no more than one buttress; and
wherein the no more than one buttress comprises a knee buttress coupled to a portion of the interior surface such that an orientation and position of the coupled knee buttress are configured to apply pressure to the subject's Vastus Medialis Obliquus (VMO) to reduce a load on the subject's knee, the knee buttress having a thickness between 0.8 cm and 1.5 cm, wherein a distal end of the knee buttress is disposed a distance of 1.3 cm to 5.0 cm from the subject's patella, wherein the knee buttress is configured to extend over and apply pressure to a belly of the VMO and activate the VMO without extending over the Vastus Lateralis and without substantially extending over or applying pressure to any other part of the subject's leg or knee covered by the flexible sleeve.

17. The topical proprioceptive tube of claim 16, wherein the knee buttress is configured to apply between 15-400 millimeters Hg of pressure to the subject's muscle.

18. The topical proprioceptive tube of claim 16, wherein the knee buttress includes a set of opposing parallel sides and a set of opposing rounded sides.

19. The topical proprioceptive tube of claim 16, wherein the knee buttress is between 4.0 centimeters (cm) and 7.6 cm wide and between 5.0 cm and 10.1 cm long.

20. The topical proprioceptive tube of claim 16, wherein a continuous and uniform portion of the interior surface is configured to receive a buttress.

* * * * *